United States Patent
Brehm et al.

[11] Patent Number: 5,972,177
[45] Date of Patent: Oct. 26, 1999

[54] PROCESS FOR PRODUCING PROTEIN HYDROLYSATES

[76] Inventors: Josef Brehm, Tannenstrasse 1, Gars, Germany, D-83555; Claus Berndt, Heufelder Strasse 31, Bad Aibling, Germany, D-84043; Klaus-Peter Stengele, Eichenweg 17, Pleinskirchen, Germany, D-84568; Winfried Kolbeck, Plantschweg, Munich, Germany, D-81247

[21] Appl. No.: 08/952,735
[22] PCT Filed: Apr. 1, 1997
[86] PCT No.: PCT/EP97/01642
§ 371 Date: May 20, 1998
§ 102(e) Date: May 20, 1998
[87] PCT Pub. No.: WO97/36500
PCT Pub. Date: Oct. 9, 1997

[30] Foreign Application Priority Data

Mar. 28, 1996 [DE] Germany .......................... 196 12 281

[51] Int. Cl.⁶ .................................................. B01J 19/08
[52] U.S. Cl. .................. 204/164; 435/70.1; 435/70.3; 435/173.2
[58] Field of Search ................................ 204/164, 165; 435/70.1, 70.3, 173.1, 173.2

[56] References Cited

FOREIGN PATENT DOCUMENTS

| 37 13 179 | 11/1988 | Germany . |
| 4231914 | 3/1994 | Germany . |
| 1692 503 | 11/1991 | U.S.S.R. . |

*Primary Examiner*—K. Mayekar
*Attorney, Agent, or Firm*—Hazel & Thomas, P.C.

[57] ABSTRACT

The invention relates to a method for producing protein hydrolyzates from animal and/or vegetable starting materials by comminuting the starting materials, mashing the comminuted starting materials into a pumpable mass, decomposing the mashed starting materials in an electric discharge gap and separating the aqueous phase of the decomposition from solid and water-unmixable residues, wherein the starting material is decomposed at a pH value between 10.0 and 14.0 and the decomposed starting material is subjected to a secondary reaction over at least 1 h at a pH value of 10.0 to 14.0, the temperature being at least 70° C.

12 Claims, 1 Drawing Sheet

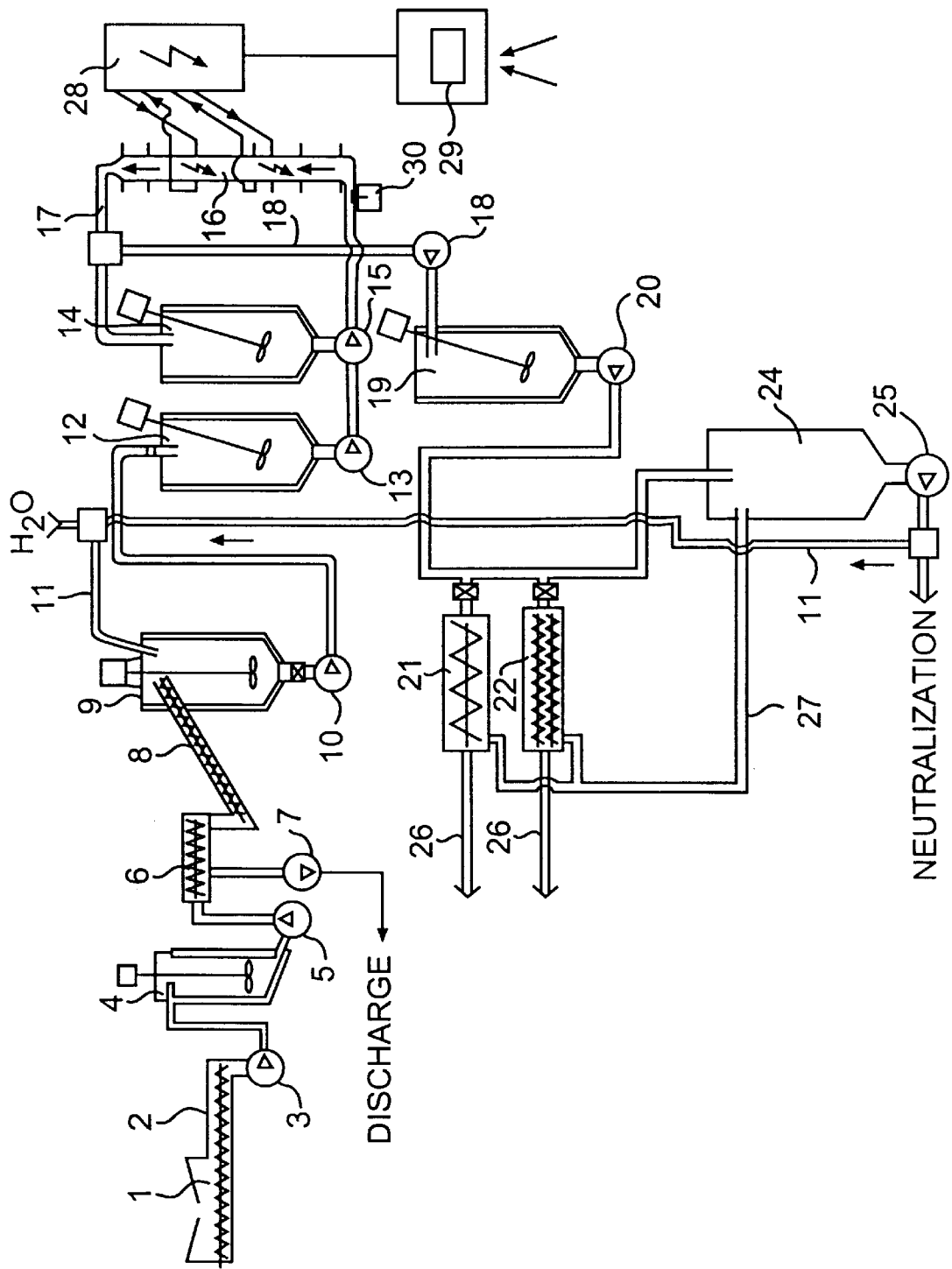

PROCESS FOR PRODUCING PROTEIN HYDROLYSATES

This application is a 35 U.S.C. 371 National Stage Filing of PCT/RP97/01642, filed Apr. 1, 1997.

BACKGROUND OF THE INVENTION

1. Field of the Invention

This invention relates to a method for producing protein hydrolyzates from animal and/or vegetable starting materials by comminuting and mashing the comminuted starting materials into a pumpable mass, decomposing the mashed starting materials in an electric discharge gap and separating the aqueous phase of the decomposition from solid and water-unmixable residues.

Protein-containing residues from industrial or manual processing of agricultural products as well as vegetable raw materials are valuable raw products due to the contained ingredients. However, a problem is frequently the cost-effective and simple recovery of these ingredients. In particular offal, such as skins, hairs, bristles, feathers, bones, meat parts, blood, etc., largely defies simple and cost-effective further processing as far as their ingredients are concerned. The contained proteins are a valuable source of raw materials hitherto utilized only to a small extent.

2. Description of the Related Art

The inventive method develops a technique known from DE 42 31 914 A1. This print describes a method for producing protein hydrolyzates from animal and/or vegetable substrates by comminuting the substrates, heating the comminuted substrate, mashing the heated substrate into a pumpable mass, decomposing the mashed substrate by means of electric discharges and separating the aqueous phase of the decomposition from solid and water-unmixable liquid residues wherein the temperature is held below the coagulation temperature of protein during the entire method and mashing is performed with aqueous hydrolyzate phase obtained from the decomposition. This method has its advantages but is still capable of being improved with respect to energy consumption and the processing of the obtained products. In particular the separation of obtained protein hydrolyzates from solid and water-unmixable liquid residues is elaborate and cost-intensive. Although one can improve the separation and subsequent filtration of the obtained hydrolyzate solution by suitable pretreating the starting materials, this is an additional step with additional costs.

DE-A 37 13 179 A1 further discloses a method for recovering gelatin and products containing it wherein collagen-containing starting material is decomposed in an aqueous medium with the aid of electric current. The collagen containing starting material used is offal. Decomposition takes place with an electric discharging current with short discharge pulses. The method obtains a collagen-containing material which is used in particular as glue.

The discharge apparatus used in this known method is known in the art and has been described for a variety of purposes, including the abovementioned. For the discharge technology reference is furthermore made to DE-PS 12 37 541 and 19 46 267 and to DE-OS 16 67 029, 17 92 572, 29 07 887 and DE 31 16 623 A1 and also to the statements in DE 37 13 179 A1.

Finally, DE-OS 27 50 149 discloses a method for producing keratin-like protein wherein keratin is hydrolyzed with saturated steam under pressure. The process conditions are quite drastic and lead to high costs and a chemically changed product.

The objectives of the invention is a method for separating the proteins contained in animal and vegetable raw materials, in particular offal and vegetable agricultural raw products and waste, in simple, cost-effective and largely pure fashion.

SUMMARY OF THE INVENTION

This objective is reached with a method of the kind described at the outset wherein the starting material is decomposed at a pH value between 10.0 and 14.0 in the discharge gap and the decomposed material is subjected to a secondary reaction for at least 1 h at a pH value of 10.0 to 14.0, the temperature being at least 70° C.

The animal raw materials that can be used are skins, hairs, bristles, feathers, bones, horn components, meat parts, blood and similar slaughter by-products. Vegetable substrates that can be used are any protein-containing vegetable products, in particular waste from agriculture and the industry processing agricultural products.

The substrates used are comminuted at the beginning of the method, for example with conventional mills, crushers, shredders and the like. The comminution should be as fine as possible since this facilitates the later decomposition of the substrates and promotes their pumpability. For this purpose the particle size should be <6–8 mm. The substrate can be cooled for example with the aid of liquid nitrogen and then ground mechanically.

The comminuted substrates can be heated in the next step to a temperature below the coagulation temperature of protein, preferably to a temperature below about 70° C. This can prove advantageous with very fatty starting materials since the existing fatty components are thereby separated, being removed from the method by skimming, draining or decanting. With low or normal fatty components, however, this step is normally unnecessary.

Then the substrate is mashed into a pumpable mass, using water or, if high product concentrations are desired, aqueous hydrolyzate phase obtained from the decomposition. Mashing with water has proven expedient in practice.

One then adds to the mashed substrate a base which increases the pH value to the desired value of pH 10.0 to 14.0 and the electric conductivity of the mass. One can further add electrolytes if still necessary. These electrolytes should enter into no chemical compounds with the substrate or the products and can be separable from the mixture by simple methods. One can use for example inorganic salts or organic compounds soluble in the aqueous phase, for example common salt or cinnamic acid. Sufficient electric conductivity is normally given by the base, however. Sodium hydroxide solution is preferably used. Lime milk can be used if the selected processing method (filtration) allows.

The mashed substrate is then decomposed by the action of electric pulses in a discharge gap. The electric pulses break/open the cells and release contained protein which is converted into the aqueous phase. The proteins themselves are polarizable as amphoteric substances and are cleaved hydrolytically under the influence of the current pulses so that they are split into a peptone mixture or even individual amino acids, possible only after several passes. In this way substantially pure protein is extracted from the substrate used, leaving the other components substantially in solid or suspended form or as a fatty phase.

When passing through the discharge gap the mashed starting materials are heated. The temperature should be held below 95° C., in particular at a final temperature in the range of 70 to 85° C. The temperature can be regulated in effective fashion by the flow rate, which is generally adjusted to values between 1.5 and 5 l/min, preferably 2 to 4 l/min. High flow rates can make it necessary to increase the number of passes through the discharge gap, i.e. to circulate the mashed starting material.

During decomposition the pH value of the material is expediently in the range of 11.0 to 13.5, whereby it should be taken into account that decomposition itself generally decreases pH value. The pH value should be selected so high that it is still within the range at the end of decomposition.

The electric discharge gap and the decomposition caused therein are followed by a secondary reaction performed at a pH value of 10.0 to 14.0 over a time period of at least 1 h and a temperature of at least 70° C. The pH value is expediently in the range of 11.0 to 13.5, whereby the temperature can be increased to a value of 95° C. The secondary reaction time is preferably 2 h to 15 h. It has proven advantageous in practice to perform the secondary reaction over night.

The secondary reaction further decomposes the material treated in the discharge gap. In particular the combination of basic pH value and high temperature results in a further separation of existing fatty components, which can be decanted or pumped off as fatty phase floating on the surface subsequent to the secondary reaction time. Solid components sediment, which is conducive to the subsequent separation process.

Subsequent to the secondary reaction the decomposed substrate is supplied to a separation zone in which the solid components are first pressed off and the aqueous phase then collected.

The aqueous phase is neutralized before further treatment, the pH value preferably being set to a value of 5.5 to 7.0, in particular about 6.5. Any acids can be used for neutralization but the use of sulfuric acid is preferred.

The neutralized product is filtered, preferably at a temperature of 50 to 80° C., in particular 65 to 75° C., microfiltration being preferred to attain a sterile product. Subsequent to filtration the product is dewatered, for example by evaporation of the aqueous phase at normal or reduced pressure, by freeze drying or spray drying.

The mashed substrate optionally mixed with an electrolyte is preferably decomposed by the electric pulse method in a discharge gap known in the art. A high voltage is produced by a generator. High-performance capacitors are used to produce discharges in the microsecond range, for example 5 to 30 discharges per second, which are applied to the substrate mixture via electrodes disposed in pairs on the discharge gap. The discharges themselves have a duration of microseconds. For the technique reference is made to the prints stated at the outset.

During decomposition, protein embedded in the substrate and contained collagens are detached from the cellular structure, leave the cell and pass into aqueous solution. The pulse surges of the discharge gap are controlled so that no burning or impermissible temperature increase occurs. Temperature monitoring is thus advantageous. In case of an impermissible temperature increase the pulse count can be reduced, the flow rate of the mash increased or the mash passing through the discharge gap cooled, for example by cooling means disposed in or after the area of the discharge gap or a separate cooling zone. The temperature of the mashed starting material is preferably adjusted before admission to the discharge gap so that the temperature increase occurring during decomposition leads to a final temperature in the permissible range.

The inventive method is preferably performed continuously. Raw material is continuously introduced, mashed and basified by the addition of lye.

The discharge gap used is preferably a vertically disposed pipe having electrodes disposed in pairs on its inner side. The electrodes are made for example of graphite. The substrate preferably passes through the discharge pipe from the bottom to the top, the flow rate being 1 to 5 l/min.

To improve decomposition to the point of free amino acids one can pass the mashed starting material through the discharge gap several times, for example up to four times, whereby a circulation method can be used. However, one pass is normally sufficient under the inventive process conditions.

If a circulation method is used, preferably about 10 to 50 wt %, in particular about 25 wt %, of the circulating treated material is transferred out and replaced by fresh mashed material. The transferred out material is treated further for recovering the aqueous hydrolyzate phase, the circulating material enriched with fresh material being passed through the discharge gap again.

The aqueous hydrolyzate phase obtained by pressing off the solid residues and/or filtration is neutralized and processed into solid product, unless it is recycled into the mashing tub in order to mash fresh material. In the mashing tub 10 to 50%, preferably about 25%, fresh material is preferably mixed with 50 to 90%, preferably about 75%, aqueous hydrolyzate phase.

The obtained hydrolyzate is converted in the way known in the art into a powder or paste which can be used for example as a basic material for the chemical, pharmaceutical or food industry, or else as fodder in agriculture.

The hitherto applied methods for recovering the protein building blocks from animal or vegetable starting materials were all based on the use of acids or enzymes and/or increased pressure and temperature. The inventive method recovers protein building blocks from the cellular substance with electricity under basic conditions. When acids and increased pressure/temperature conditions are used changes in the protein building blocks or amino acids cannot be avoided so that a less pure product is (frequently) obtained. The use of enzymes is extremely expensive and not selective in every case. According to the invention, by contrast, the release of amino acids is obtained without an adverse chemical change. Aromatics, starches and sugars released together with the protein building blocks can be separated off with separation methods known in the art, and the amino acid mixture split up in the usual way.

The protein building blocks recovered in the inventive method are available pure, depending on decomposition and separation need. The hydrolyze obtained according to the invention has a dry substance content of up to 40 wt % of peptones and/or amino acids. Known methods based on the addition of external water reach a dry substance content of 3 to at most 10%. The product obtained according to the invention is, after drying, a pourable and substantially odorless sterile powder or paste.

The cellular parts, keratins, tissue structures, lignin substances and residual materials not composed in the inventive method can be processed further into fodder or fertilizer after being conveyed off/pressed off.

The invention involves a number of advantages relating to the entire process control. The procedure in the strongly basic range at increased temperature facilitates the separation of fatty components during processing. One can thus also include rather fatty material in the method and normally do without a fat separation stage in the preparation. This considerably simplifies the plant and also saves energy costs since the hearing required for fat separation in the preparation can be dispensed with.

In addition, the treatment time in the discharge gap is altogether shorter since hydrolysis is promoted by the basic milieu. The base serves simultaneously as an electrolyte so that one can normally dispense with additives increasing the conductivity of the mash. The shortened treatment time allows the number of passes through the discharge gap to be reduced so that just one pass and accordingly long after-treatment can usually obtain a sufficiently decomposed product.

In addition, the inventive procedure increases the pumpability of the mash so that one can work with high concentrations of starting material.

The invention will be explained more closely with reference to the enclosed figure.

BRIEF DESCRIPTION OF THE DRAWING

The animal or vegetable starting material is first supplied to comminuting means, for example a usual grinder or shredder. Comminution should ensure a particle size of less than 6 to 8 mm, a more extensive reduction of the starting material being conducive to the method since it increases the pumpability of the mash and the enlarged surface facilitates decomposition. Comminution generally takes place at ambient temperature or with cooling, but heating can also be performed at 2, in particular with very fatty materials, in order to permit a preliminary separation of the fat.

The following method steps are helpful in particular for treating very fatty material with heating but are not absolutely necessary for the success of the inventive method. The continued material will thereby be heated at 2.

The starting material is introduced with thick matter pump 3 into mixing vessel 4 with a heater and stirrer, homogenized there and heated to the process temperature. The thus homogenized material is passed with thick matter pump 5 into separating apparatus (decanter) 6 in which fat and water are separated and supplied to further processing by means of pump 7. A twin-shaft press can also be used instead of a decanter.

The material leaving separating apparatus 6 is conveyed via worm 8 into receiving tank 9 with a stirrer. Aqueous hydrolyzate phase can be introduced into tank 9 via return pipe 11 for mashing the heated and defatted material. Alternatively and preferably, however, mashing is done with water.

From receiving tank 9 the mashed substrate passes via pump 10 into metering vessel 12 to the pulse zone, said vessel having a stirrer and a metering device for sodium hydroxide solution. From metering vessel 12 the mashed material is then passed with the aid of metering pump 13 to pulse zone 16 with the discharge elements. The pulse zone can have a plurality of discharge elements, or a plurality of pulse zones can be connected in parallel or in series.

The decomposition process initiated in the pulse zone takes place continuously. From receiving tank 9 raw material is supplied continuously via metering vessel 12.

The pulse zone preferably consists of a vertically disposed pipe that is passed from the bottom to the top. Metering pump 13 and dosing pump 15 for circulating material ensure a conducive flow rate of 1 to 5 l/min, whereby the throughput can be monitored and controlled via flow monitor 30 so that the particular required dwell time and the temperature are maintained. The temperature can also be controlled via a cooling device.

In order to obtain full decomposition under the gentlest conditions with respect to the applied current strength in accordance with the pulse count per second, the material flowing through the pulse zone can be circulated. It flows through the pulse zone several times, preferably up to four times depending on the requirement, 25% mashed raw material is supplied via mashing tub 9, 75% of the material treated in the pulse zone is kept in circulation, and 25% of the particular circulating quantity is transferred out.

The material leaving pulse zone 16 passes into pipe 17 which forks, leading into circulation vessel 14 with a stirrer and heater or cooling means, on the one hand, and via removal pipe and pump 18 into secondary reaction vessel 19, on the other hand. Via removal pump 18 preferably 10 to 50% and in particular about 25%, of the decomposed substrate is taken out of circulation.

The material reaching circulation vessel 14 is recycled into pulse zone 16 via material pump 15. The circulating quantity itself is determined by the material fed by metering pumps 13 and 15 in coordination with flow monitor 30 and control means. 75% circulating material and 25% admixed mashed starting material is particularly preferred.

Secondary reaction vessel 19 receives the material decomposed in the discharge gap. A stirrer makes sure that material can be kept moving, and a hating device, in particular one permitting regulated temperature control via a heating jacket by means of steam, ensures the optimal temperature for the secondary reaction in the range of 70 to 95° C. Temperature and pH value are monitored and readjusted if necessary. For this purpose a metering device for sodium hydroxide solution can be present which raises a reduced pH value back into the range of 10 to 14. Under the given process conditions it has turned out that decomposition continues and a phase separation quickly occurs into a fatty phase floating on top, an aqueous phase containing peptones and amino acids, and a bottom sedimentation phase. In this phase the pH value, which can drop greatly in the discharge gap, generally remains more or less constant.

The material is secondary reaction vessel 19 transferred out of the method via removal pump 18 passes via pump 20 into a preliminary separation in which the fatty phase is separated off and solute and nonsolute separated from each other. The fatty phase is preferably separated with decanter 21, the solid components in preliminary filter 22, substances being discharged from each at 26 and aqueous hydrolyzate passing via pipe 27 into hydrolyzate vessel 24. Hydrolyzate vessel 24 is connected via pump 25 and return pipe 11 with receiving tank 9 in which starting material can be mashed with hydrolyzate to the point of pumpability.

From hydrolyzate vessel 24 the hydrolyzate then passes into a preferably heated neutralization stage in which the hydrolyzate is neutralized or slightly acidified (pH 6.5) with sulfuric acid. Neutralization is followed by usual sterilization by filtration. The material sterilized by filtration is then dewatered and supplied to further use.

The obtained hydrolyzate is completely sterile and can be further processed and in particular processed into the individual amino acids by known methods. The hydrolyzate itself is absolutely sterile and contains virtually only the particular amino acids and/or peptones after decanting, pressing and filtering.

The high voltage for pulse zone 16 is produced with the aid of generator 28. The current is applied to the discharge gap in microsurges via a chopper and high-performance capacitors. Control and checking are effected via oscillograph 29 for the current strength and the pulse count per unit of time. The current is discontinuous direct current. It can be a pulsed current or discharging current, the latter being produced via capacitors. Capacitors with a capacitance of 5 to 25 $\mu$F and a pulse frequency of 5 to 30 pulse/s have proved especially favorable. High voltage in a range of 2 to 20 kV is preferably used. The field strength is dependent on the diameter of the pulse zone and dependent on quantity. The voltage can be up to 100 kV in plants with an hourly capacity of 8 to 10 t. Voltage, pulse sequence and pulse duration are varied in accordance with the material used so that the protein components of the substrate are decomposed into the individual amino acids as completely as possible.

The obtained hydrolyzate is free from microorganisms, in particular with sterilization by filtration. With conventional methods this sterility and this result of work were only reached by working with time, pressure of acids.

The amino acids in the hydrolyzate are separable and enter into no new bonds through the stated method.

EXAMPLE 1

In the plant shown in the figure 300 kg pork rind ground to $\leq 0$ mm was mashed with 15 l 25% sodium hydroxide solution and mixed thoroughly. The initial pH value was 12.2. The initial temperature was 25° C., which was increased by heating and the heat transferred in the pulse zone to a value $\geq 70$ and <80° C.

The mixture was passed through the pulse zone for 2 hours at a rate of 200 kg/h. The voltage was 5.1 kV, the current strength 3.0 A, the capacitance 25 $\mu$F and the resistance 2.4 ohms. The pH value remained substantially constant, the mixture itself became increasingly liquid and better pumpable.

After the end of decomposition the mixture as subjected to a secondary reaction with the stirrer running, the temperature being increased from initially 75° C. to 92° C. The pH value as brought to 12.05 with 50 l NaOH, and the mixture first stirred vigorously for 3 hours.

The mixture was then left to stand over night. Separation occurred into a lower aqueous and an upper fatty phase; altogether 170 l aqueous phase and 120 l fatty sludge were obtained by decanting. The latter was discarded.

The aqueous phase was brought to a pH value of 6.5 with 15% $H_2SO_4$ and then subjected at a temperature of 80 to 82° C. to microfiltration at a rate of initially 36 l/h. Altogether 175 l solution sterilized by filtration was obtained; 35 l residue was left.

A pourable powder was obtained by evaporating the residual water.

EXAMPLE 2

230 kg freshly butchered pork rind was ground to $\leq 6$ mm and brought to a pH value of 11.3 with 40 l sodium hydroxide solution. After homogenization and adjustment of the temperature to 75° C. the mixture was guided through the pulse zone at a rate of 90 to 100 kg/h in two consecutive passes. In the first pass the temperature was increased from 20° C. to 75° C., in the second pass to 80° C. The pH value remained constant at 11.3. The pulse zone as operated with a voltage of 3.4 kV and a current strength of 5 A (1.5 A in the second pass). The capacitance was 30 $\mu$F, the resistance 20 $\Omega$ (15 $\Omega$ in the second pass).

Decomposition was over after about 5 hours, after which rinsing was performed with 40 l water and a pH value of 11.3 again set with sodium hydroxide solution. The stock was left to stand at 75° C. over night, then screened to 0.5 mm and decanted. The aqueous phase, altogether 200 l, was set with sulfuric acid to a pH value of 5.8 and then microfiltered under pressure as described in Example 1. The yield of aqueous solution was 74 wt %, including sodium hydroxide solution, and 26% fatty water.

We claim:

1. A method for producing protein hydrolyzates from animal and/or vegetable starting materials, said method comprising the steps of comminuting the starting materials, mashing the comminuted starting materials into a pumpable mass, decomposing the mashed starting materials in an electric discharge gap at a temperature of less than 95° C. and at a pH value between 10.0 and 14.0, separating an aqueous phase of the decomposed mashed starting materials resulting therefrom from solid and water-unmixable residues and subjecting the decomposed mashed starting materials to a secondary reaction over at least 1 hour at a pH value of 10.0 to 14.0 and a temperature of at least 70° C.

2. The method of claim 1, wherein said decomposing is performed at a temperature in the range of 70° C. to 85° C.

3. The method of claim 1, wherein the pH value is in the range of 11.0 to 13.5 during decomposition.

4. The method of claim 1, wherein the secondary reaction is performed at a temperature of up to 95° C.

5. The method of claim 4, wherein the secondary reaction is performed at a temperature of 75° to 90° C.

6. The method of claim 1, wherein the secondary reaction is performed at a pH value of 11.0 to 13.5.

7. The method of claim 1, wherein the secondary reaction time is 2 to 15 hours.

8. The method of claim 1, wherein sodium hydroxide solution is used as a base for setting the pH value.

9. The method of claim 1, wherein the mashed starting materials are decomposed by electric pulse method at a voltage of more than 2 kV with a pulse frequency of 5 to 30 pulse/s, and a flow rate in the pulse zone of 1 to 5 l/min.

10. The method of claim 1, wherein the starting materials are mashed with water.

11. The method of claim 1, wherein the separated aqueous phase is brought with an acid to a pH value of 5.0 to 7.0 and then sterilized by filtration at a temperature of 50° C. to 90° C.

12. The method of claim 1, wherein the separated aqueous phase is dried in a spray tower.

* * * * *